(12) United States Patent  (10) Patent No.: US 8,067,246 B2
Marlborough et al.  (45) Date of Patent: *Nov. 29, 2011

(54) DIAGNOSTIC TESTING PROCESS

(75) Inventors: David Ian Marlborough, Balgowlah (AU); Andrew John Sloane, Balmain (AU); Robert Alan Cole, Greenwich (AU); William Samuel Hunter, Jan Juc (AU)

(73) Assignee: Tyrian Diagnostics Limited, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/874,675

(22) Filed: Sep. 2, 2010

(65) Prior Publication Data

US 2010/0323369 A1  Dec. 23, 2010

Related U.S. Application Data

(63) Continuation of application No. 10/497,925, filed as application No. PCT/AU02/01684 on Dec. 12, 2002, now Pat. No. 7,875,435.

(30) Foreign Application Priority Data

Dec. 12, 2001  (AU) .................................. PR 9451
Jul. 11, 2002  (AU) .............................. 2002950212

(51) Int. Cl.
*G01N 33/543*  (2006.01)

(52) U.S. Cl. ........ 436/518; 422/401; 422/402; 422/408; 422/420; 422/425; 422/430; 435/287.2; 435/287.7; 435/287.9; 435/288.5; 435/810; 435/973; 436/514; 436/810

(58) Field of Classification Search .......................... None
See application file for complete search history.

(56) References Cited

U.S. PATENT DOCUMENTS 4,233,402 A   11/1980  Maggio et al.
(Continued)

FOREIGN PATENT DOCUMENTS

EP  0 447 154 B1  9/1991
(Continued)

OTHER PUBLICATIONS

Verheijen, R., "Development of a One Step Strip Test for the Detection of (Dihydro)streptomycin Residues in Raw Milk," *Food and Agricultural Immunology* 12:31-40 (2000).

(Continued)

*Primary Examiner* — Chris L Chin
(74) *Attorney, Agent, or Firm* — Hamilton, Brook, Smith & Reynolds, P.C.

(57) ABSTRACT

A method and apparatus for use in a flow through assay process is disclosed. The method is characterised by a "pre-incubation step" in which the sample which is to be analyzed (typically for the presence of a particular protein), and a detection analyte (typically one or more antibodies bound to colloidal gold or a fluorescent tag) which is known to bind to the particular protein may bind together for a desired period of time. This pre-incubation step occurs before the mixture of sample and detection analyte come into contact with a capture analyte bound to a membrane. The provision of the pre-incubation step has the effect of both improving the sensitivity of the assay and reducing the volume of sample required for an assay. An apparatus for carrying out the method is disclosed defining a pre-incubation chamber for receiving the sample and detection analyte having a base defined by a membrane and a second membrane to which a capture analyte is bound. In one version the pre-incubation chamber is supported above the second membrane in one position but can be pushed into contact with the membrane carrying the capture analyte thus o permitting fluid transfer from the incubation chamber through the capture membrane. In another version the membrane at the base of the incubation chamber is hydrophobic and its underside contacts the capture membrane and when a wetting agent is applied to the contents of the pre-incubation chamber fluid transfer occurs.

20 Claims, 6 Drawing Sheets

U.S. PATENT DOCUMENTS

| | | | |
|---|---|---|---|
| 4,246,339 A | 1/1981 | Cole et al. | |
| 4,299,916 A | 11/1981 | Litman et al. | |
| 4,366,241 A | 12/1982 | Tom et al. | |
| 4,391,904 A | 7/1983 | Litman et al. | |
| 4,435,504 A | 3/1984 | Zuk et al. | |
| 4,623,461 A | 11/1986 | Hossom et al. | |
| 4,632,901 A | 12/1986 | Valkirs et al. | |
| 4,693,834 A | 9/1987 | Hossom | |
| 4,877,586 A | 10/1989 | Davaney et al. | |
| 4,912,034 A | 3/1990 | Kalra et al. | |
| 4,916,056 A | 4/1990 | Brown, III et al. | |
| 4,956,302 A | 9/1990 | Gordon et al. | |
| 5,008,080 A | 4/1991 | Brown et al. | |
| 5,137,691 A | 8/1992 | Parker | |
| 5,149,622 A | 9/1992 | Brown et al. | |
| 5,167,924 A | 12/1992 | Clark | |
| 5,185,127 A | 2/1993 | Vonk | |
| 5,366,867 A | 11/1994 | Kawakami et al. | |
| 5,391,478 A | 2/1995 | Greene et al. | |
| 5,514,602 A | 5/1996 | Brooks et al. | |
| 5,571,667 A | 11/1996 | Chu et al. | |
| 5,658,801 A | 8/1997 | Poissant et al. | |
| 5,710,049 A | 1/1998 | Noppe et al. | |
| 5,763,262 A | 6/1998 | Wong et al. | |
| 5,885,526 A | 3/1999 | Chu | |
| 6,057,165 A | 5/2000 | Mansour | |
| 6,312,888 B1 | 11/2001 | Wong et al. | |
| 6,565,808 B2 | 5/2003 | Hudak et al. | |
| 7,205,159 B2 * | 4/2007 | Cole et al. | 436/518 |
| 7,875,435 B2 * | 1/2011 | Marlborough et al. | 435/7.32 |
| 2002/0064888 A1 | 5/2002 | Maynard et al. | |
| 2003/0049857 A1 | 3/2003 | Chan | |
| 2003/0207442 A1 | 11/2003 | Markovsky et al. | |
| 2005/0164404 A1 | 7/2005 | Marlborough | |

FOREIGN PATENT DOCUMENTS

| | | |
|---|---|---|
| EP | 0 319 294 B1 | 10/1994 |
| EP | 0 651 249 A2 | 5/1995 |
| WO | WO 96/07099 | 3/1996 |
| WO | WO 96/35123 | 11/1996 |
| WO | WO 97/06437 | 2/1997 |
| WO | WO 98/13519 A1 | 4/1998 |
| WO | WO 98/32018 | 7/1998 |
| WO | WO 99/36773 | 7/1999 |
| WO | WO 99/64863 | 12/1999 |
| WO | WO 00/55626 | 9/2000 |
| WO | WO 01/84153 A2 | 11/2001 |
| WO | WO 02/31465 A1 | 4/2002 |
| WO | WO 03/016902 A1 | 2/2003 |

OTHER PUBLICATIONS

International Search Report for PCT/AU2002/001684, date of mailing Mar. 11, 2003.

International Preliminary Examination Report for PCT/AU2002/001684, completion date of report Feb. 6, 2004.

International Search Report for PCT/AU2002/01119 date of mailing Nov. 25, 2002.

Abdel-Hamid, I., et al., "Flow-through immunofiltration assay system for rapid detection of *E. coli* O157:H7," *Biosensors Bioelectornics*, 14 3(L 309-316 (1999).

Gennaro, M.L., "Immunologic Diagnosis of Tuberculois," *Clinical Infectious Diseases*, 30 (Suppl. 3): S243-S246 (2000).

* cited by examiner

DIAGNOSTIC TESTING PROCESS

RELATED APPLICATIONS

This application is a continuation of U.S. application Ser. No. 10/497,925, now U.S. Pat. No. 7,875,435, filed Feb. 3, 2005, which is the U.S. National Stage of International Application No. PCT/AU2002/001684, filed on Dec. 12, 2002, published in English, and claims priority under 35 U.S.C. §119 or 365 to Australian Application No. 2002950212, filed Jul. 11, 2002 and Australian Application No. PR9451, filed Dec. 12, 2001.

The entire teachings of the above applications are incorporated herein by reference.

FIELD OF THE INVENTION

This invention relates to a diagnostic testing process and in particular to an apparatus for use in carrying out an assay process and to a method of carrying out an assay process using that apparatus.

BACKGROUND OF THE INVENTION

Background Art

Lateral flow and flow-through technology have been used for diagnostic assays for almost twenty years. Lateral flow technology is currently dominant because lateral flow devices are easy to produce and the assay can be performed in a simple 2-step process that can be adapted for whole blood separation. This results in a simple device that can be used in the field as a rapid point-of-care diagnostic (Cole et al 1996 Tuberc. Lung. Dis. 77: 363-368). However, multiple disease diagnosis using lateral flow technology is very difficult because of differences in lateral diffusion between samples and variation in flow rates between batches of the partitioning membrane. This means that antigen or antibody signal strengths may vary both within tests and between batches of tests, resulting in inconsistent results.

Existing flow-through diagnostic tests can be completed in less than two minutes compared with typical times of five to fifteen minutes for lateral flow tests. This advantage in speed however, is often at the expense of sensitivity. A further disadvantage is that higher volumes of sample are required to achieve the same sensitivity as lateral flow. This may be problematic in some situations. For example, the diagnosis of analytes (reagents) in whole blood requires the separation of plasma from whole blood cells. The higher volumes of whole blood required for this would quickly block the membranes in the flow-through format.

The basic principal of flow-through assays is well established. The tests are designed to determine the existence of, and in some cases, the quantity of, a predetermined analyte/reagent in a sample. Often the reagent will be a protein but other reagents can be tested for. If the assay is to test for the existence of a particular disease in a patient, the patient's body fluids may be tested for an antibody or other protein produced by the patient in response to the infection, or for a protein which is expressed by the bacterium or viral agent or the like causing the disease. In a typical flow through assay a liquid sample which is believed to contain the reagent is sucked into an absorbent pad via a membrane to which is bound a capture analyte which is known to bind to the reagent. The membrane is then typically washed with a buffer and a liquid containing a detection analyte which also binds to the reagent and which includes a tracer or marker which is detectable, is applied to the membrane. The detection analyte binds to the immobilised reagent bound to the membrane and can be seen or otherwise detected to indicate the presence of the reagent.

U.S. Pat. No. 4,246,339 discloses a test device for assaying liquid samples for the presence of a predetermined reagent. The device includes telescoping top and bottom members defining a liquid reservoir therebetween and resilient means for biasing the members in the open position. The top member defines a series of test wells each of which has a base defined by a microporous membrane with a capture analyte immobilised on the membrane surface. Absorbent means are located in the bottom member, spaced from the membrane in the open position but in contact therewith in the closed position. U.S. Pat. No. 4,246,339 discloses adding the test serum diluted with a buffer to a test well, and incubating the device at room temperature for ten minutes prior to depressing the cassette to the closed position to pass the sample through the membranes into the absorbent material. When the membranes are dry, the membrane is washed and then covered with a solution containing a detection analyte which binds to the immobilised reagent followed by a subsequent step in which a stain is applied.

It will be appreciated that the process described in U.S. Pat. No. 4,246,339, is a somewhat long drawn out, time consuming and tedious process and also lacks sensitivity.

A more recent flow through device is described in U.S. Pat. No. 5,185,127 which discloses an assay device including a filter stack and an enclosure having a base portion and a lid. The filter stack has a hydrophilic membrane having a capture analyte thereon, referred to in U.S. Pat. No. 5,185,127 as a binder. A hydrophobic membrane is located under the hydrophilic membrane and a pad of absorbent material is located under the hydrophobic membrane. The lid includes an upwardly extending rib which defines a recess having an insert therein. In use, a sample containing the reagent (referred to in U.S. Pat. No. 5,185,127 as the analyte) is placed in the well of the assay device at which time the reagent/analyte binds to the capture analyte/binder. Flow of the assay solution however, does not take place because the aqueous solution does not wet the hydrophobic membrane placed under the hydrophilic membrane in the filter stack. Thus as much time is necessary to complete the binding of the detection analyte to the reagent is allowed. When binding is judged to be complete, flow may be initiated by adding a wetting agent which wets the hydrophobic membrane. After which time the aqueous liquid flows into pad of absorbent material. The membrane may then be washed and treated with a detection analyte/tracer which may be an antibody which specifically binds to the analyte, the antibody having a label overtly conjugated thereto. Again the sensitivity of U.S. Pat. No. 5,185,127 is lacking and is not equivalent to that obtainable in lateral flow or ELISA formats.

General Information.

As used herein the terms "derived from" or "derivative" shall be taken to indicate that a specified integer may be obtained from a particular source albeit not necessarily directly from that source.

Unless the context requires otherwise or specifically stated to the contrary, integers, steps, or elements of the invention recited herein as singular integers, steps or elements clearly encompass both singular and plural forms of the recited integers, steps or elements.

The embodiments of the invention described herein with respect to any single embodiment and, in particular, with respect to an apparatus or a method of assaying shall be taken to apply mutatis mutandis to any other embodiment of the invention described herein.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally-equivalent products, compositions and methods are clearly within the scope of the invention, as described herein.

The present invention is performed without undue experimentation using, unless otherwise indicated, conventional techniques of immunocytochemistry such as for example immunogold labeling and proteomics. Such procedures are described, for example, in the following texts that are incorporated by reference:

Colloidal Gold-A New Perspective For Cytochemical Marking, Beesley J (1989), Royal Microscopical Society Handbook No 17. Oxford Science Publications. Oxford University Press. (Paperback);

An Introduction To Immunocytochemistry: Current techniques and problems, Polak J and Van Noorden 5 (1984) Royal Microscopical Society Handbook No 11. Oxford Science Publications. Oxford University Press. (Paperback);

Immunocytochemistry-Modern Methods and Applications, Polak J and Van Noorden 5 (1986) (2nd ed), Butterworth Heinemann, Oxford. (Hardback);

Techniques in Immunocytochemistry, Bullock G and Petmsz P (1982-1989) (4 volumes) Academic Press. (Paperback); and Colloidal Gold-Principles, Methods and Applications, Hayat M, (1989-1990) (3 volumes), Academic Press. (Hardback).

All the references cited in this application are specifically incorporated by reference herein.

Because the prior art is not consistent in its terminology, for the avoidance of doubt and for the purpose of clarity, the following terms used in the specification below, are defined as follows. The term "reagent" or "target analyte" is used to refer to a macromolecule (eg. protein or enzyme) or fragment thereof, or the like which is to be detected by an assay. The term "capture analyte" is used to refer to a "capture" compound which is bound to a membrane and to which the reagent will bind. The term "detection analyte" is used to refer to an analyte which comprises a "detection" compound which will also bind to the reagent and also a "detectable" element. The detectable element is typically visually detected whether under visible light, or fluorescence.

SUMMARY OF THE INVENTION

In a first broad aspect, the present invention provides an apparatus and method for use in an assay process which is characterised by providing a "pre-incubation step" in which a reagent and detection analyte may bind together, which has the effect of both improving the sensitivity of the assay and reducing the volume of sample required for an assay prior to reaction of the sample/analyte complex with a reaction membrane to which one or more ligands are bound.

In one embodiment, the detection analyte is a multi-detection analyte comprising more than one detection compound bound to a detectable element.

Thus, in one aspect of the present invention there is provided an apparatus for use in an assay process comprising:

a first member comprising a first, porous, reaction membrane to which is bound a capture analyte for binding to a reagent to be detected, the member having an upper surface and a lower surface;

a second member being a body of absorbent material such as tissue paper or the like disposed below and touching the lower surface of the first member;

a chamber spaced above the first member said chamber having side walls, and a base defined by a second membrane; and means for supporting the chamber above the first member in two positions, a first position in which the membrane is spaced a sufficient distance from the first member so as to not permit fluid transfer from the chamber to the body of absorbent material, and a second position in which the membrane is in contact with the first member thus permitting fluid transfer from the chamber through the first and second membranes to the body of absorbent material.

In a related aspect the present invention provides a method for assaying for the presence of a pre-determined reagent using an apparatus of the present invention comprising the steps of:

a) placing a sample to be assayed and a detection analyte in the chamber, with the chamber disposed in the first position;

b) allowing a sufficient period of time to pass for the detection analyte to bind to the reagent, if present;

c) depressing the chamber to the second position to contact the base of the chamber with the first porous membrane, d) allowing the sample to flow through the first and second membranes to allow the reagent, if present to bind to the capture analyte carried on the first membrane, preferably wherein the detection analyte is a multi-detection anlayte.

As used herein "multi-detection analyte" refers to a detection analyte which comprises more than one detection compound bound to a detectable element.

The inventors have surprisingly found that a multi-detection analyte has a number of advantages according to the present invention including, any of the following, for example, multiple-detection compounds can be bound to detectable elements at optimum binding efficiency, detection analytes produced with multiple detection compounds have a similar size and physical characteristics for each of the detection compounds, the ratio of detection compounds on the detectable element can be altered without affecting relative binding profiles of the detectable element, quantitative comparisons can be performed, and the detectable element has a reduced capacity for nonspecific binding.

Accordingly, in a preferred embodiment the invention provides a method for assaying for the presence of at least one pre-determined reagent comprising the steps of:

a) providing a first porous membrane to which capture analytes for binding to the at least one reagent have been bound;

b) placing a sample to be assayed and a multi-detection analyte in a chamber having a base defined by a second porous membrane;

c) allowing a sufficient period of time to pass for the multi-detection analyte to bind to the at least one reagent, if present;

d) contacting the base of the chamber with the first porous membrane; and e) causing the sample to flow through the membranes to allow the reagent to bind to the capture analyte carried on the first membrane.

Preferably, the detection compound is an antigen, antibody, or ligand.

Antibodies, antigens and ligands can be used as detection compounds as they have binding sites capable of specifically binding to the proteins of interest or fragments or epitopes thereof in preference to other molecules.

Antibodies are obtainable from a commercial source, or alternatively, produced by conventional means. Commercial sources will be well known to those skilled in the art.

As used herein the term "specifically bind" with reference to a complex-forming agent such as an antibody, refers to the agent preferentially associating with a target analyte (eg. protein of interest). With respect to antibodies in particular, it is recognised that a certain degree of non-specific interaction may occur between a molecule and a non-target protein. Nevertheless, specific binding may be distinguished as mediated through specific recognition of the antigen.

In alternate embodiments, the detection compound (antibody or ligand) is linked to an element to detect target analyte in a sample by directly or indirectly labelling the antibody or ligand, (e.g. with radioactive, fluorescent or enzyme labels, such as horseradish peroxidase) so that they can be detected using techniques well known in the art. Directly labelled analytes have a label (detectable element) associated with or coupled to the detection compound. Indirectly labelled detection elements may be capable of binding to a labelled species (eg. a labelled antibody capable of binding to the developing agent) or may act on a further species to produce a detectable result.

Detectable elements can be conjugated to antibodies (or other ligands) and include macromolecular colloidal particles (e.g. colloidal gold particles) or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. In one embodiment, the detection compound (antibody) is conjugated to a colloidal gold particle. Binding of the conjugated antibody to the sample protein produces a visual signal that can be detected by eye or read electronically to give a quantitative result. Biotin/avidin or biotin/streptavidin and alkaline phosphatase detection systems may also be employed.

Other labels are known to those skilled in the art.

Preferably, the detection element is selected from the group comprising colloidal gold particle, latex bead, coloured dye and colloidal carbon.

In one embodiment, the detectable element is colloidal gold. Preferably the colloidal gold provides uniform reflectance properties.

In an alternate embodiment, the detectable element is a latex bead linked to a coloured dye.

In another embodiment, the detectable element is colloidal carbon.

Preferably, a positive result is where the signal from a "test" sample in the assay is significantly higher or lower than a sample from a control sample.

Thus, the present invention provides a chamber which may serve as a pre-incubation chamber which a pre-incubation step can occur where the sample and multi-detection analyte combine, which improves the sensitivity of the test and reduces the volume of sample required for the assay. It has been found that the pre-incubation step increases the test sensitivity for a typical existing flow-through apparatus by approximately ten times to equivalent levels of sensitivity compared with lateral flow technology, while still allowing the assay to be completed in around two minutes compared to 10 minutes for lateral flow formats.

In one embodiment the sample is selected from or is derived from the group comprising: agricultural product, microbial product, and biological product.

In one embodiment, the agricultural product is selected from the group comprising a seed, grain or plant extract.

In one embodiment, the sample contains particulate materials selected from the group comprising grain extract, cell extract and microbial extract.

In an alternate embodiment, the biological sample is a bodily fluid or tissue sample selected from the group comprising: blood, serum, sputum, and lung.

Other samples are not excluded.

Standard methods can be used to obtain, prepare and/or store samples for use in the present invention. For example, in one embodiment an adsorbent swab comprising a cotton matrix or similar material can be used to probe or surface or medium that may contain a target analyte. In one embodiment, the adsorbent swab is washed to remove the target analyte. Preferably, the target analyte and/or the particulate material comprising the target analyte is then solubilised.

Accordingly, in one embodiment a ground wheat head suspension can be solubilised, and then mixed and pre-incubated in the chamber with a multi-detection analyte comprising a primary antibody against alpha-amylase linked to a colloidal gold particle and a control secondary antibody also linked to the colloidal gold particle. The contents of the chamber are then allowed to flow through to the first membrane containing a capture analyte in the form of an immobilised anti-amylase antibody, or anti-control antibody and antibody/gold complexes will bind to the immobilised antibody forming a detectable signal. The signal can be detected by the removal of the pre-incubation unit and washing of the reaction membrane with buffer.

In another embodiment the invention can also be used for detecting reagents in whole blood since whole red blood cells can be removed in the pre-incubation chamber and the plasma allowed to flow-through to the reaction membrane containing a bound capture analyte. In this format, the base membrane defined at the base of the pre-incubation chamber will typically be a membrane which has the correct pore size to retain the red blood cells and allow the plasma to pass through on contact with the first membrane. Similarly particulate samples containing grain extracts, cell or microbial extracts can be analysed with this flow-through format since particulate matter can be removed in the pre-incubation chamber and therefore cannot block the reaction area on the upper surface of the reaction membrane.

The apparatus can also be used for detecting analytes in body fluids other than blood, such as plasma, sera, urine, saliva and sputum. In this case, the sample can be retained in the pre-incubation chamber by use of a hydrophobic membrane. To obtain efficient flow through capillary action to the second member when the pre-incubation chamber is lowered, the reaction membrane is pre-wet with a wetting agent containing a detergent or the reaction membrane is blocked with a hygroscopic solution such as sucrose, trehalose, fructose, or alternatively, glycerol.

This changes the characteristics of the reaction membrane from a non-hygroscopic to a hygroscopic membrane allowing the sample to flow through to the second member upon contact of the membrane at the base of the pre-incubation chamber with the reaction membrane.

In a yet further embodiment, if a hydrophobic membrane is used as the base of the pre-incubation chamber, the apparatus may be used with the hydrophobic membrane and reaction membrane in contact, with the operator adding a wetting agent to the sample to cause flowthrough, when desired.

Thus, in a related aspect, there is provided an apparatus for use in an assay process comprising a housing including:

a first member comprising a first, porous, membrane to which is bound a capture analyte for binding to a reagent to be detected, the member having an upper surface and a lower surface;

a second member being a body of absorbent material such as tissue paper or the like disposed below and touching the lower surface of the first member;

a chamber located above the first member said chamber having side walls, and a base including a second, hydrophobic, membrane, having an upper and a lower surface, the pre-incubation chamber being supported above the first member with the lower surface of the hydrophobic membrane in contact with the upper surface of the first member.

The pre-incubation chamber can also be used to remove analytes that may interfere with the assay, such as human. anti-mouse antibodies (HAMAS), in solution or by binding anti-analyte antibodies to the surface of the chamber. The chamber can also be used to extract the analyte of interest from an absorbent surface such as a swab, which has been taken from the throat of a patient, by swirling the swab in an extraction solution in the chamber. The pre-incubation chamber may be part of a pre-filter unit which acts also to pre-filter the sample prior to contact with the upper surface of the first member.

Examples of assays that can be performed by this method where two reaction steps are involved (the incubation of the analyte with the labeled anti-analyte followed by the binding of this complex to a solid-phase anti-analyte), are:

Direct Antigen Assay
1. $Ag^*$(analyte)+$Ab^*_1$(anti-Ag)-label
2. Solid phase-$Ab_2$(anti-Ag)+$Ag$/$Ab_1$(anti-Ag)-label complex Direct Antibody Assay (i)
1. $Ab_1$(analyte=anti-Ag)+$Ab_2$(anti-$Ab_1$)-label
2. Solid phase-$Ag$+$Ab_1$(anti-Ag)/$Ab_2$(anti-$Ab_1$)-label complex Direct Antibody Assay (ii)
1. $Ab_1$(analyte=anti-Ag)+$Ab_2$(anti-$Ab_1$)-label
2. Solid-phase-$Ab_3$(anti-Ag)/$Ag$+$Ab_1$(anti-Ag)/$Ab_2$(anti-$Ab_1$)-label complex Indirect Antigen Assay
1. $Ag$ (analyte)+$Ab_1$(anti-Ag)+$Ab_2$(anti-$Ab_1$)-label
2. Solid-phase-$Ab_3$(anti-Ag)+$Ag$/$Ab_1$(anti-Ag)/$Ab_2$(anti-$Ab_1$)-label complex Indirect Antibody Assay (i)
1. $Ab_1$(analyte=anti-Ag)+$Ab_2$(anti-$Ab_1$)+$Ab_3$(anti-$Ab_2$)-label
2. Solid phase $Ag$+$Ab_1$(anti-Ag)/$Ab_2$(anti-$Ab_1$)/$Ab_3$(anti-$Ab_2$)-label complex Indirect Antibody Assay (ii)
1. Abt (analyte=anti-Ag)+$Ab_2$(anti-$Ab_1$)+$Ab_3$(anti-$Ab_2$)-label
2. Solid phase $Ab_4$(anti-Ag)/$Ag$+$Ab_1$(anti-Ag)/$Ab_2$(anti-$Ab_1$)/$Ab_3$(anti-$Ab_2$)-label complex

*Ag indicates antigen
*Ab indicates antibody

Alternate types of assays are not excluded.

A piezoelectric driven printer may be used to dispense precise amounts of multiple disease ligands such as antigens or antibodies or an analyte as a micro array onto a reaction membrane for use in the apparatus of the first aspect of the present invention. The ligands or analytes may be dispensed in particular patterns, e.g. letters for ease of recognition of results. Typically, 100 pl of fluid reagent (1 drop), or multiples thereof, is dispensed, but this will vary depending on the application. The resultant size of the spot on the membrane is about 55 microns or more in diameter subject to fluid diffusion on the membrane, but again this will vary depending on the application. It is possible to dispense droplets with diameters of 5-10 microns, and hence lower volumes of fluid reagent (for example, 1-10 pl) can be applied. Using precise quantitative printing of micro arrays of antibodies, antigens, or other analytes means that tests using precise quantities of these reagents can be produced for multi disease diagnosis of a single sample. This array technology can be applied to tests for drugs or other markers across all diagnostic fields.

Alternatively, an adult/neonatal syringe pump 1235 from ATOM Medical Corporation, Japan, typically used to administrator small quantities of intravenous liquids through a catheter to hospital patients can be adapted to apply single or multiple lines of a capture analyte to the first membrane eg nitrocellulose.

In one preferred embodiment, ligands for detecting tuberculosis, HIV, hepatitis, syphilis and malaria antibodies may be deposited onto a reaction membrane. This would allow the simultaneous diagnosis of tuberculosis, HIV, hepatitis, syphilis and malaria from a single blood sample without the need for intermediate sample treatment steps.

Utilising the present invention allows the assaying of small volumes of whole blood and thus the present invention provides a very rapid diagnostic assay device that is simple to use and can be used in both laboratory and point-of-care field diagnostic locations. For example, a finger prick of blood would be sufficient to perform an assay. Similarly large volumes of sample can be used in this device by increasing the amount of absorbent material (second member). For instance, 10 mls of dilute fluids like urine can be can be assayed to detect low abundance molecules.

Analytes and/or ligands (e.g. antigens or antibodies) can be printed down in titrating amounts and/or concentrations. Thus, in an individual screen, this would provide a means of quantitating analyte-ligand levels within the sample solution.

BRIEF DESCRIPTION OF THE DRAWINGS

A specific embodiment of the present invention will now be described by way of example only and with reference to the accompanying drawings in which.

DETAILED DESCRIPTION OF THE INVENTION

Preparation of Detection Analyte

Figure 1:
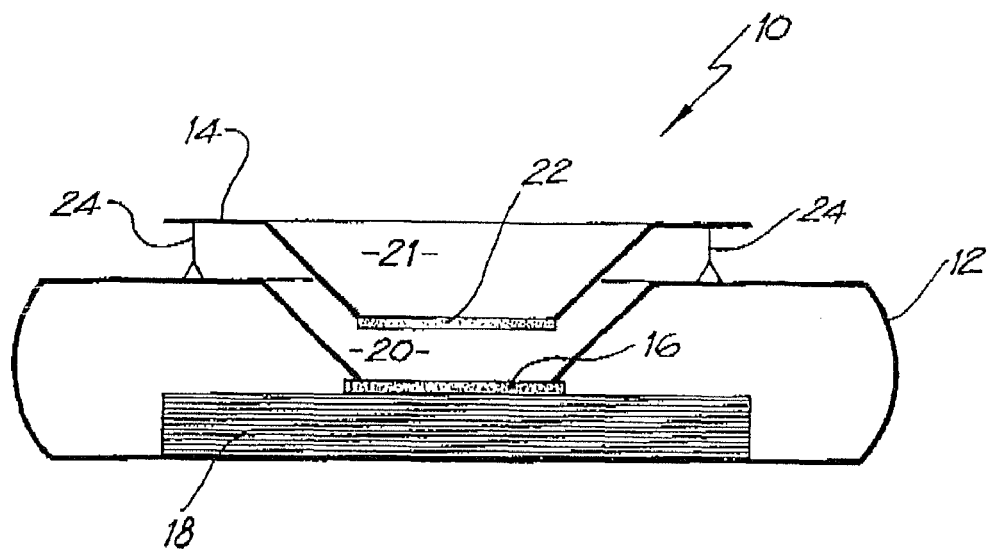
FIG. 1 is a schematic drawing of an apparatus embodying aspects of the present invention in a first configuration.

The entities bound to a gold colloid to produce the immunogold conjugate (normally immunoglobulins) are passively bound to give a stable complex that retains the target activity of the antibody. The native gold colloid dispersion as produced at Proteome Systems Limited (PSL) is initiated with hydroxylamine reducing agent. Based on the assumption that the oxime is partially retained as a moiety in the colloid, the immunogold conjugate is stabilised by addition of glutaraldehyde in the binding step to form a Schiff's base between any residual oxime in the colloid structure and free amines from the immunoglobulin.

The optimum binding profile for the immunoglobulin (concentration and pH) is obtained by titration of the antibody concentration against fixed aliquots of gold colloid at specific pH values and treatment of the mixtures with saline solution. A sufficient concentration ratio for binding between colloid and antibody prevents flocculation or aggregation of the colloid from suspension when treated with the saline solution. Hence at low protein concentrations the addition of the saline results in the colloid aggregating out of suspension, but when the optimum level of antibody is reached the colloid remains stable in suspension (the integrity of the colloid suspension is measured spectroscopically between wavelengths of 450 nm and 600 nm) This value of antibody concentration gives the minimum protecting concentration required to form the stable immunogold conjugate complex. An antibody concentration of 0.1 to 0.2 mg/mL in 5 mM borate is used in the titration and for polyclonal antibodies a pH of 9 is chosen: this pH is normally is well above the range of isoelectric point (pI) values encountered with the range of immunoglobulins in a polyclonal serum. In the case of monoclonal antibodies from a hybridoma the immunoglobulins have a unique isoelectric point and the pH of the colloid is usually set at 0.5 to 1 unit above the pI of the antibody.

The concentration of antibody used for the conjugation is 110% of the minimum 'protecting' concentration determined from the titration procedure described herein.

Conjugation Protocol (for Single Antibody)

The required volume of colloid is measured out (assuming a 90% yield the volume is nearly equivalent to that of the final conjugate at the optical density measured for the colloid).

A volume of 5% glutaraldehyde solution is added to the rapidly-stirred colloid to give a final glutaraldehyde concentration of 0.002%.

Five minutes after addition of the glutaraldehyde the calculated amount of antibody solution is added to the rapidly-stirred suspension. If a significant volume of antibody is to be added (>10 mL) it is added in a steady stream of drops (preferably through a dropping funnel).

After 30 to 90 minutes depending upon the volume of colloid (from 200 mL to 5 L) the pH of the suspension is taken down from pH 9 to pH 7 (unless the conjugation is carried out between pH 7.5 to 6) with 0.2M phosphoric acid.

A calculated volume of 10% (w/v) bovine serum albumin is added to the suspension to give a final concentration of bovine serum albumin in the suspension of 0. 5%. The suspension is left stirring for 3 to 4 hours or overnight when the volume is >1 L and then centrifuged at 10,000 rpm for between 35 minutes and 60 minutes (depending upon volume and colloid size).

The supernatant is removed from the centrifuged suspension and the concentrated liquid centrifugate taken up in 2 mM borate at pH 7.2 containing 0.2% bovine serum albumin and 0.1% sodium azide (as preservative).

Conjugation Protocol (for Multiple Antibodies)

For more than one antibody bound to the colloid, the protecting concentration titrations (probed with saline for aggregation) are carried out for each of the antibodies. The volumes of antibodies used are those found for the individual antibodies (+10%) from the titrations.

If equivalent binding levels of the antibodies at their individual optimum binding levels are required, the antibodies are pre-mixed and added together to the colloid (after glutaraldehyde addition). The processing follows the procedure then described above for single conjugations. If the antibodies are required to be at a particular ratio to each the primary antibody is added first and the secondary antibodies added at intervals later. The time course of the binding levels to the colloid have been determined for some combinations of antibodies and the levels of the second and subsequent antibodies decrease in a regular pattern with the time interval between addition of the first antibody and subsequent additions. After 30 to 40 minutes interval a constant level of the second antibody bound at approximately 10% of the primary reactant level is found. In some cases an interval of 5 minutes between test antibody and procedural control antibody at the required concentration ratios is found to be optimal.

In one example, the primary antibody is mouse anti α amylase conjugated at pH 8.3, and the secondary antibody (control) is goat immunoglobulin G. In another example, two primary antibodies (eg. anti-Human IgG1 and anti-Human IgG2) can be added simultaneously and a control antibody added at a suitable interval afterwards.

Preparation of Membrane with Capture Analyte

Capture analytes in the form of ligands such as antigens or antibodies (e.g. TB, HIV-1) are printed onto a protein-capture membrane matrix (e.g. a nitrocellulose membrane) in an appropriately sized array using piezoelectric chemical printing technology. A suitable chemical printing system for use in the present invention involves the use of piezoelectric drop-on-demand ink jet printing technology for micro-dispensing fluids in DNA diagnostics or the Combion Inc. synthesis process called "CHEM-JET". To explore drop on demand fluid dispensing for DNA diagnostics, an eight fluid printer has been developed as part of the Genosensor Technology Development (GTD) project funded by the Institute of Standards and Technology (USA). Research to date, is focused on printing oligonucleotide micro-spots onto solid supports. In the CHEM-JET technique, which was developed at the California Institute of Technology, tiny volumes of reagent bearing liquid are squirted onto specific spots or addresses of a solid substrate much as an ink-jet printer squirts ink onto a page. By repeatedly returning to each address with one or another of a small set of building blocks, in this case, nucleotides modified for the process, huge two-dimensional libraries of short DNA chains (oligonucleotides) can be assembled. Such a device including an imaging means is described in the applicant's co-pending International patent application No PCT/AU98/00265, the entire contents of which are incorporated herein by reference. In the described embodiment, antigen is printed onto a reaction membrane in 100 pl droplets, or multiples thereof (eg. 10 nl), with each aliquot being 1 mm apart. However, these volumes and distances can be increased/decreased accordingly depending on the chosen antigen titre and array size. For example, it is possible to dispense droplets with volumes as low as 1-10 pl.

In a particularly preferred embodiment, antigens or antibodies can be printed down in a matrix of dots or lines or in the shape of letters so that quantitative multiple analyte analysis of a single sample is possible.

After the dispensed antigen has dried, non-specific protein-binding sites on the (nitrocellulose) membrane are blocked using 0.5% (v/v) casein in phosphate buffered saline (PBS)+ 0.05% (w/v) sodium azide+0.1% (v/v) Tween-20 (PBSA wash buffer). It is however an option to leave the membrane unblocked following the printing of the antigen (or antibody) or other ligand.

In another preferred embodiment syringe pump technology used for the administration of liquids intravenously to patients can be adapted to lay down single or multiple lines on nitrocellulose membranes.

Use of Immunoconjugates in Flow-through Format

The optical density of the immunoconjugate suspension is usually measured at a wavelength of 520 nm. This value gives a relative measure of the concentration of the colloid. Also from knowledge of the conjugation conditions the level of antibody bound to the colloid at an optical density=1 is known and this can be used to determine the optimum volume to use in the flow-through test (antibody concentration per mL of colloid x volume of conjugate x optical density of conjugate).

The immunoconjugate is added to the sample that is pre-incubated in the filter assembly prior to contact with the active membrane in the housing. This enables the maximum level of binding of the analyte in the sample to bind to the active antibody conjugated to the colloid. The conjugate: analyte complex is then captured by the immobilised test antibody on the membrane as the mixture filters through the active membrane exposed to the sample fluid at the same time as the procedural control antigen binds to the secondary antibody linked to the conjugate.

For multi-analyte samples the multiple antibodies on the conjugate (detectable element) would bind at the same level to the sample anlaytes as the conjugated antibodies would be at their optimum binding levels on the colloid particle.

Description of the Figures

Turning to the drawings, FIG. 1 shows a flow-through assay device 10, which utilises the nitrocellulose membrane described above. The device is in the form of a cassette 12 and an associated removable filter frame 14. Inside the cassette there is the membrane (typically nitrocellulose) 16 on which capture analytes in the form of ligands are printed, as described above, which is located on top of an absorbent matrix 18. The absorbent matrix preferably comprises multiple layers of absorbent tissue or an absorbent pad such as blotting paper, in the specific embodiment twenty-four layers (double ply), which have been found to possess an ideal porosity that permits the most rapid flow-through of various solutions. This rapid flow-through is important as it results in lower backgrounds with higher reaction specificity and higher signal resolution.

As shown in FIG. 1, the top of the cassette defines an opening in its upper face and a depending generally frusto-conical well whose sides depend down as far as the membrane 16, to define a chamber having sloping sides and a base defined by the membrane 16.

The filter unit frame 14 is spaced above the upper surface of the cassette 12. It also defines a depending conical well in the form of a chamber 21 also referred to as a "pre-incubation chamber" having sloping sides and a base 22 formed from a 5 µm Whatman grade 1 membrane or a 0.22 µm hydrophilic Durapore membrane filter (Millipore, North Ryde, Australia). However, other types of filter/membrane and pore size would be suitable depending on the application. The function of the membrane is to retain a sample to be assayed in the well or pre-incubation chamber 21 long enough for a "pre-incubation step" to take place. When membrane 22 is lowered to contact the membrane 16, capillary attraction draws the sample from the chamber 20 through membranes 22 and 16 and into the tissue 18.

Figure 2:
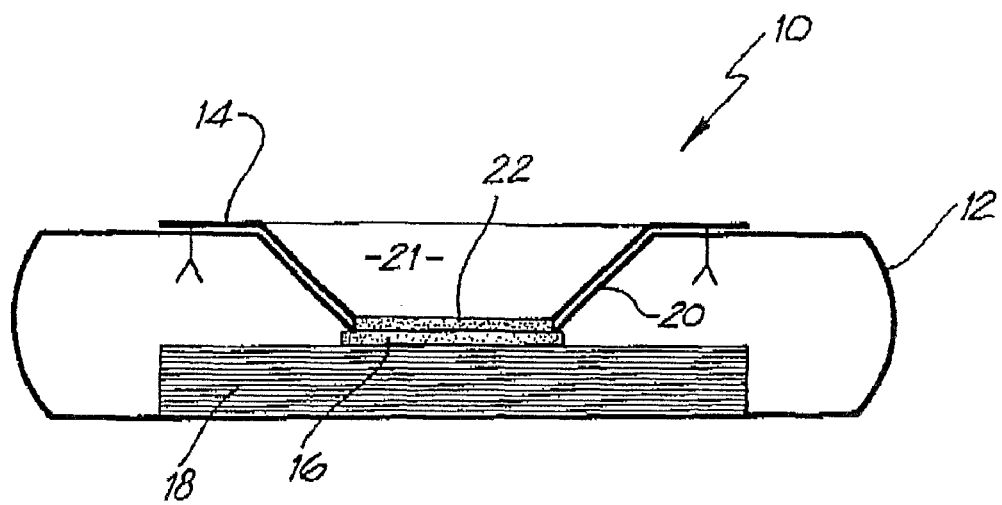
FIG. 2 is a schematic drawing of the apparatus of FIG. 1 in a second configuration.

For ease of use, two pins 24 are provided which support the filter frame 14 at an appropriate distance above the cassette 12 during the pre-incubation step but which allow the filter frame to be pushed down so that the membranes 22 and 16 are in contact for the second stage of the process shown in FIG. 2. The frame 14 is also removable so that the membrane 16 can be viewed to determine the results of the assay.

FIGS. 3 to 5d illustrate one commercial assay device design embodying the aspects of FIGS. 1 and 2.

In those Figures, the components which are equivalent to components shown in FIGS. 1 and 2 carry the same reference numerals. The cassette 12 comprises an upper moulding 12a and a lower moulding 12b. The porous membrane 22 is defined by the base of a pressed filter paper frustro cone 22a held in place by a filter retainer 23. The filter unit frame 14 defines two dimples 14a on which an operator's thumbs may press when depressing the filter frame to contact the membranes 22 and 16.

Figure 5A:
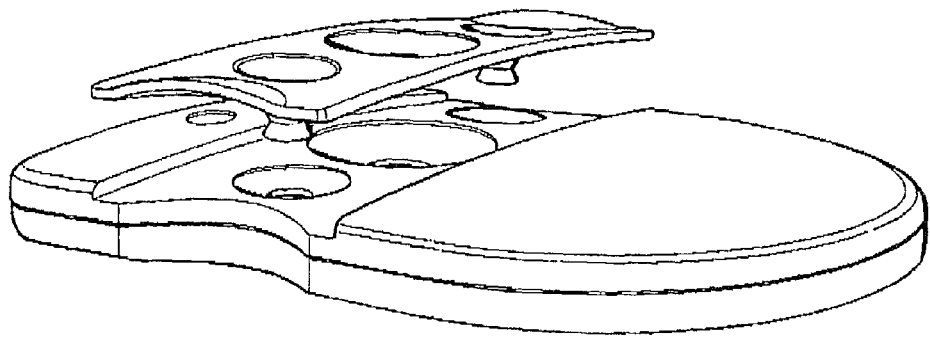
FIGS. 5a to 5d show various stages in the use of the apparatus of FIG. 3 in carrying out an assay.
Figure 5B:
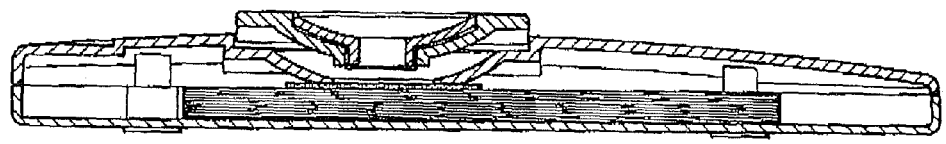
Figure 5C:
Figure 5D:
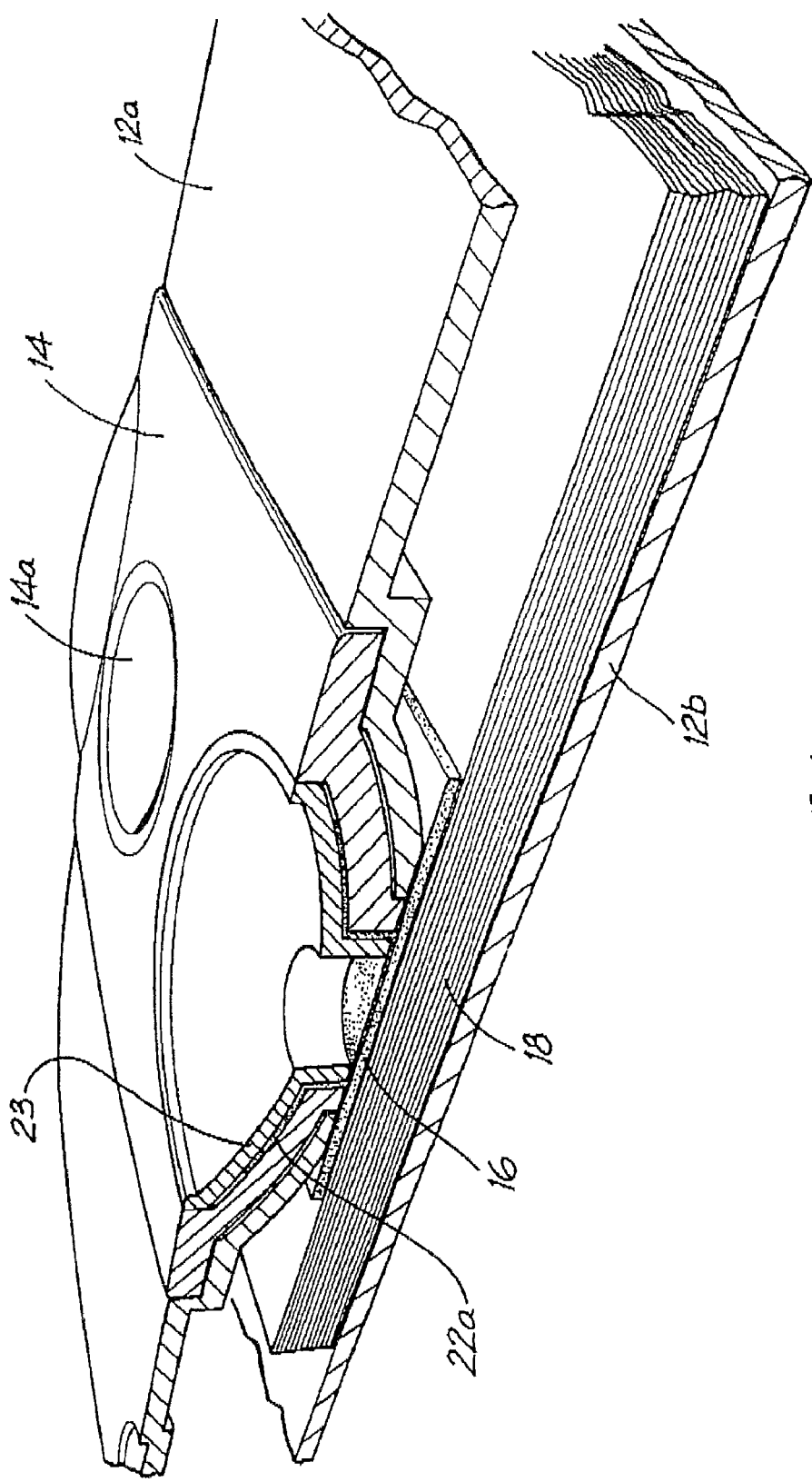
Figure 6:
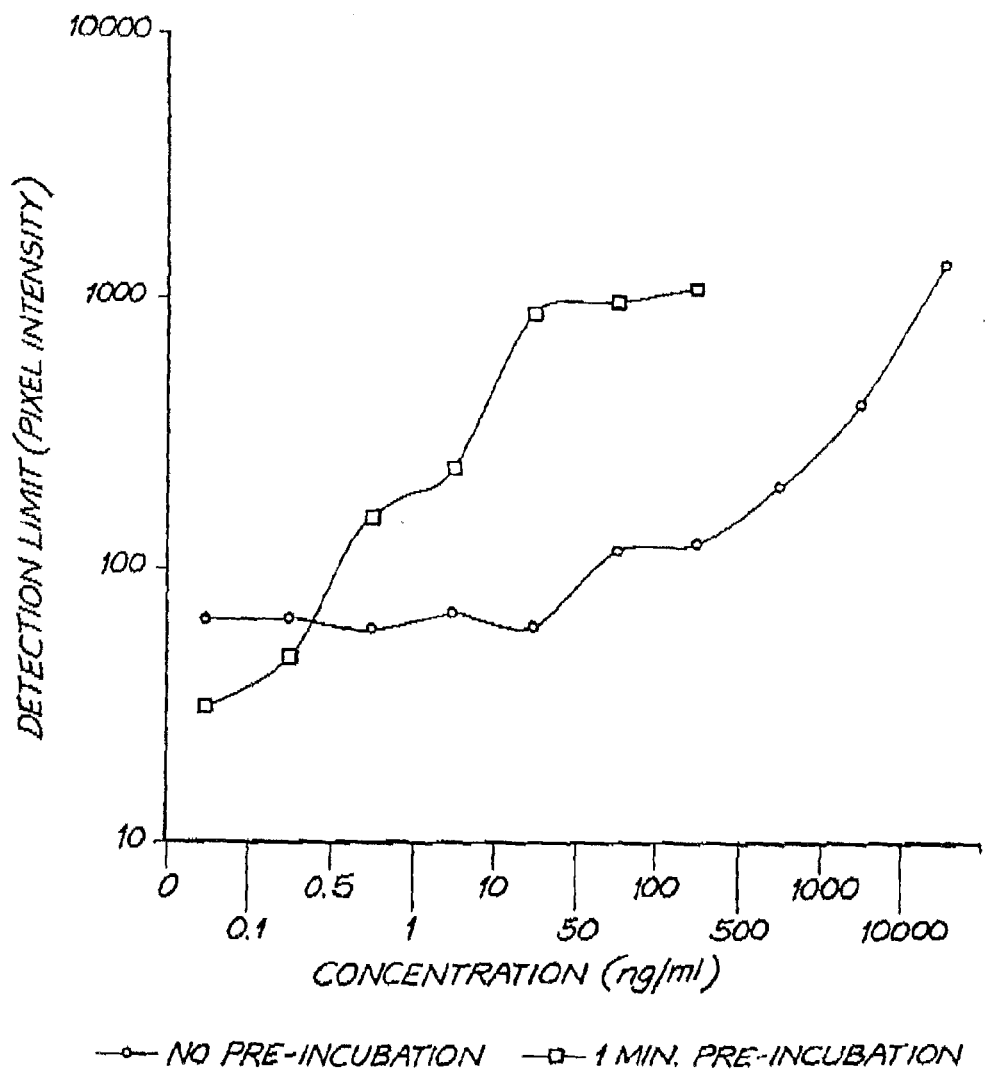
FIG. 6 is a graph comparing test results from samples spiked with alpha amalyse undergoing no-pre-incubation with samples undergoing a one minute pre-incubation.

FIGS. 5a to 5d illustrate the stages of operation of the apparatus. FIG. 5a illustrates the filter frame separate from the cassette 12. FIG. 5b illustrates the pre-incubation positioned with the base of the chamber/well 21 spaced from membrane 16. FIGS. 5c and 5d illustrate the device after the filter unit has been pressed down to bring the membranes 22 and 16 into contact to allow the sample to flow through to the blotting paper 18.

Figure 3:
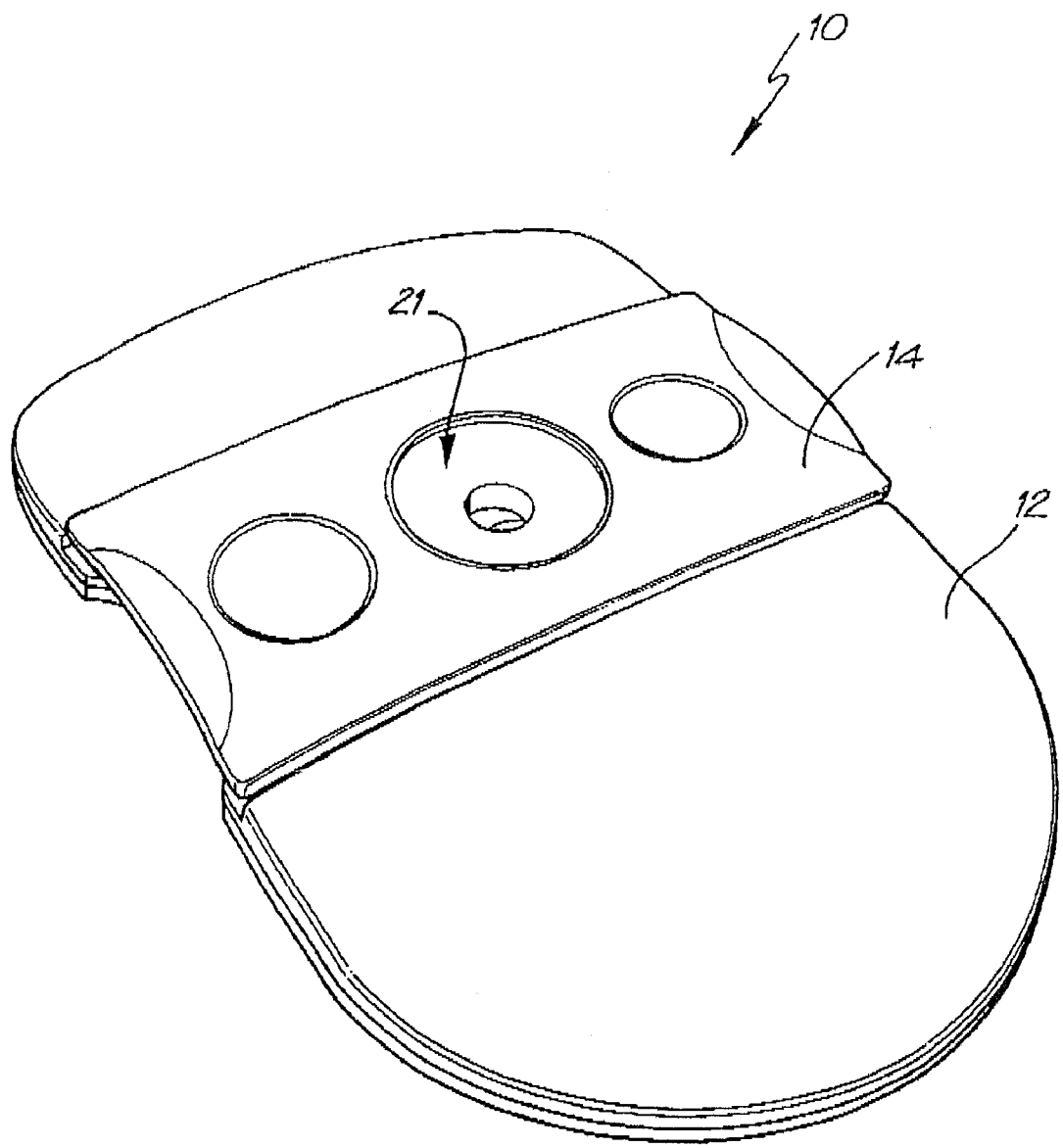
FIG. 3 is a perspective view of an assay apparatus or cassette embodying aspects of the present invention.
Figure 4:
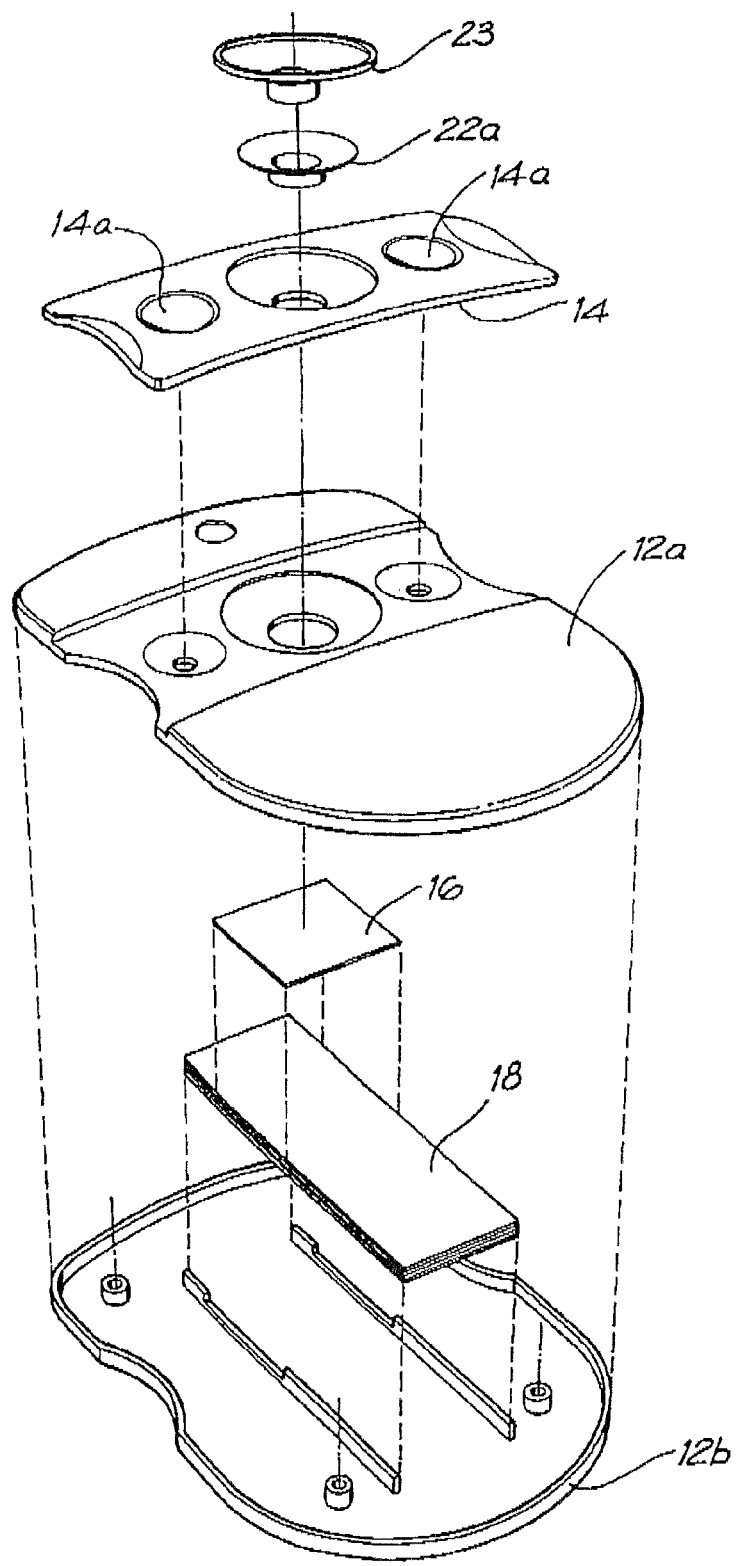
FIG. 4 is an exploded view of the components of the cassette shown in FIG. 3.

If the membrane 22 is replaced with a hydrophobic membrane, it is possible to operate the device with a pre-incubation step solely in the position shown in FIGS. 3 and 4 with the membranes 22 and 16 always in contact. The hydrophobic membrane 22 will prevent flow of the sample in the incubation chamber 21 to the reaction membrane 16. After a sufficient period of time has past for detection analyte in the chamber 21 to bind to the reagent, a suitable wetting agent is added to the sample in the chamber which allows the sample to flow through the hydrophobic membrane past the reaction membrane 16 and into an absorbent matrix 20.

EXAMPLE 1

Application of the Pre-Filter Chamber

Whatman membrane (paper) or Reemay filters (polyester; 1 cm$^2$) are inserted into the chamber 21 in the filter frame to form a conical retaining vessel (pre-filter unit).

The sample is pipetted into the plastic pre-filter chamber (50-100 µl) along with a detection analyte in the form of a detecting antibody (50-100 µl) bound to colloidal gold (particle size 20-50 nm). The sample is pre-incubated with the gold-conjugate (O.D.4) within the pre-incubation chamber for thirty seconds after gentle pippetting to ensure adequate mixing. After thirty seconds the chamber is pressed into the well 20 of the test cassette 12. Upon contact with the membrane 16 containing the detection zone, the solution filters through to the absorbent layer 18 beneath. The pre-filter 14 is discarded when the solution has filtered through and two drops of PBSA wash buffer are then added to the reaction membrane to wash away excess gold-conjugate revealing the results of the assay on membrane 16.

The use of the pre-incubation of the sample with the detection analyte increases sensitivity by approximately ten fold. Further, any particulate matter is retained in the pre-incubation chamber all of which can be removed to provide a clear signal. The use of the preincubation chamber with the dual roles of permitting a pre-incubation step and a pre-filtering step, also allows multi-analyte detection on the reaction membrane by pre-incubating with a multi-analyte probe, e.g. colloidal gold bound to different detecting analytes. In addition, interfering analytes or substances that could cause false positives or negatives in the assay can be removed or absorbed out in the pre-incubation step, e.g. human antibodies to mouse antigens can be absorbed out by anti-HAMA antibodies.

Although the above described example relates to the antigens relating to disease, the immunoassay apparatus could be used, for example, as an allergy test kit, as a test kit for drugs of abuse or for analysing non-human derived samples e.g. bovine, porcine, veterinary tests, and tests in agriculture such as grain quality evaluation, etc.

The method and apparatus of the present invention is particularly suited to use with swabs which can be simply placed into the chamber 21, swirled around in liquid containing a detecting antibody (50-100 ul) bound to colloidal gold for 30 seconds before the pre-filter unit is depressed to contact the membranes 22 and 16 together.

Any combination of ligands and analytes can be applied to the system of the present invention. The choice of ligands could be tailored to detect prevalent diseases in a particular country or population. For example, analytes from the following combination of diseases could be used for diagnosis using this array.

1. TB and HIV
2. Hepatitis-B & C, HIV
3. Chagas, HIV, TB, Syphilis and Hepatitis-B & C
4. Malaria, Dengue, TB, Chagas.

Alternatively antigens representing different varieties of wheat or other agricultural products could be printed on the reaction membrane enabling detection of multiple strains with a single test.

EXAMPLE 2

The assay device can also be used for detecting analytes in body fluids other than blood such as plasma, sera, urine, saliva and sputum. In this system, the sample can be retained in the pre-incubation chamber 22 by use of a hydrophobic membrane such as Reemay or Hollingsworth and Vose 7303 instead of the Whatman grade 1 membrane or a 0.22 μm hydrophilic Durapore membrane filter described above. The sample is mixed with the detection analyte for the required pre-incubation period. To obtain efficient flow through capillary action to the absorbent layer 18 when the pre-incubation chamber 22 is lowered onto the cassette 12, one of two procedures can be followed:

1. The membrane 16 containing the capture analyte is pre-wet with at least one drop of wash buffer containing 0.01 M phosphate, 0.15 M NaCl, 0.0% Azide, 0.5% Tween 20 or any wetting agent containing a detergent;
2. The membrane 16 containing the capture analyte is blocked with a hygroscopic solution such as sucrose, trehalose, fructose, or alternatively, glycerol. This changes the characteristics of the membrane 16 from a non-hygroscopic to a hygroscopic membrane allowing the sample to flow through to the absorbent layer 18 upon contact of the membrane at the base of the pre-incubation chamber 22 with membrane 16.

EXAMPLE 3

Comparative Example

Comparison of 'No Pre-Incubation and 1 Minute Pre-Incubation of a Sample Spiked with Alpha Amylase in the Above Described Format
Procedure A 6% solution of bovine sera albumin was spiked with 0.1 ng/ml, 0.5 ng/ml, 1 ng/ml, 10 ng/ml, 50 ng/ml, 100 ng/ml, 500 ng/ml and 1000 ng/ml and applied to the above format according to the following procedure:
No-Preincubation I. The pre-incubation chamber was pressed down so that the base of the chamber comes into contact with the first member containing the capture antibody against alpha amylase.
II. Sixty microliters of 0.5% tween in saline was added to the pre-incubation chamber and allowed to filter through to the absorbent material beneath the first membrane.
III. One hundred microliters of spiked alpha amylase sample was added to the chamber and allowed to filter through to the absorbent material beneath the first membrane.
IV. Sixty microliters of 0.5% tween in saline was added to the pre-incubation chamber and allowed to filter through to the absorbent material beneath the first membrane.
V. Sixty microliters of anti-alpha amylase antibody linked to colloidal gold (particle size 20-50 nm) was added to the pre-incubation chamber and allowed to filter through to the absorbent material beneath the first membrane.
VI. Sixty microliters of 0.5% tween in saline was added to the pre-incubation chamber and allowed to filter through to the absorbent material beneath the first membrane.
VII. The pre-incubation chamber was removed and the result on the reaction membrane scanned with a densitometer. Signal strength was measured in pixel intensity.

One Minute Pre-Incubation
I. Sixty microliters of 0.5% tween in saline was added to first membrane and allowed to filter through to the absorbent material underneath.
II. The pre-incubation chamber was suspended over the first membrane so that there was a space between the chamber and the membrane.
III. One hundred microliters of spiked alpha amylase sample and 60 microliters of anti-alpha amylase antibody linked to colloidal gold (particle size 20-50 nm) were incubated in the pre-incubation chamber for 1 minute.
IV. The chamber was lowered until it came in contact with the first membrane and the mixture of sample and antibody-gold conjugate allowed to filter through to the absorbent material.
V. Sixty microliters of 0.5% tween in saline was added to the pre-incubation chamber and allowed to filter through to the absorbent material.
VI. The pre-incubation chamber was removed and the result on the reaction membrane was scanned with a densitometer. Signal strength was measured in pixel intensity.

Each data point on the graph is the average of two experiments using the apparatus described above. The results show that pre-incubation of the sample with the detection analyte has a minimal detection limit defined in pixel density of around 500 pg/ml of alpha amylase. This is compared to a minimum detection limit without the pre-incubation of about 50 ng/ml and indicates the pre-cubation increases the sensitive by around 10 fold.

EXAMPLE 4

Comparative Examples

Demonstration of Increased Sensitivity-with Increased Pre-Incubation of the Sample with the Detection Analyte Samples of amylase diluted in 0.5% saline to 400 ng/mL were treated with immunogold conjugate against amylase and aliquotted onto the flow-through format in different protocols as shown below.
A. The sample was added to the format (without a filter present) and allowed to filter through prior to adding conjugate, followed by an aliquot of conjugate immediately the sample had passed through the membrane.
B. The sample was mixed in the correct proportions with gold conjugate and aliquotted immediately onto the flow-through format.
C. The sample was mixed as with protocol B but added to the flow through format after a 60 second interval.

The results presented in pixel intensity are shown in the tables below (for 2 experiments):

| Protocol | Sample peak | Control peak | Sample area | Control area | S/PC ratio |
|---|---|---|---|---|---|
| A | 82 | 286 | 657 | 2120 | 317 |
| B | 288 | 758 | 2062 | 5509 | 383 |
| C | 823 | 949 | 5843 | 6765 | 884 |

| Protocol | Sample peak | Control peak | Sample area | Control area | S/PC ratio |
|---|---|---|---|---|---|
| A | 89 | 516 | 588 | 3890 | 588 |
| B | 482 | 830 | 3736 | 6345 | 602 |
| C | 708 | 829 | 4506 | 5822 | 792 |

Clearly there is a significant increase in the sample signal when the analyte is preincubated with the conjugate probe, as distinct to sequential detection on the flow-through format. The difference in detection levels (for the 400 ng/mL sample) equated to between a 7.5-fold to 10-fold increase in detectable amylase in the flow through format when the sample is preincubated separately to the detecting capture antibody.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A flow-through assay device comprising:
a cassette consisting of a first member and a second member, wherein the first member defines a well having an upper surface and a lower surface wherein the upper surface of said well has an opening and the lower surface of said well is defined by a porous reaction membrane to which is bound one or more capture analytes and the second member consists of a body of absorbent material disposed below the lower surface of the first member;
a removable chamber spaced above the first member of the cassette said removable chamber having side walls and a base defined by a membrane; and
means for supporting the removable chamber above the first member in a first position and a second position, wherein the first position provides sufficient spacing between the chamber and the first member so as to not permit fluid transfer from the chamber to the body of absorbent material, and wherein the second position provides for contact between the membrane of the removable chamber and the first member to thereby permit fluid transfer from the removable chamber to the body of absorbent material.

2. The flow-through assay device as claimed in claim 1 wherein the chamber is a well.

3. The flow-through assay device as claimed in claim 1, wherein the membrane defined at the base of the chamber is a hydrophilic membrane.

4. The flow-through assay device as claimed in claim 1, wherein the membrane defined at the base of the chamber is a hydrophobic membrane.

5. The flow-through assay device according to claim 1, wherein the porous reaction membrane to which is bound one or more capture analytes is a nitrocellulose membrane.

6. The flow-through assay device according to claim 1, wherein the porous reaction membrane has bound thereto multiple capture analytes.

7. The flow-through assay device according to claim 1, wherein a capture analyte is an antigen or antibody.

8. The flow-through assay device according to claim 7, wherein the antigen or antibody is for detecting tuberculosis, HIV, hepatitis, syphilis or malaria.

9. The flow-through assay device according to claim 1, wherein the body of absorbent material consists of multiple layers of absorbent tissue or an absorbent pad.

10. A method for assaying for the presence of at least one pre-determined reagent in an assay sample, said method comprising the steps of:
a) providing a flow-through assay device consisting of:
a cassette consisting of a first member and a second member, wherein the first member defines a well having an upper surface and a lower surface wherein the upper surface of said well has an opening and the lower surface of said well is defined by a porous reaction membrane to which is bound one or more capture analytes and the second member consists of a body of absorbent material disposed below the lower surface of the first member;
a removable chamber spaced above the first member of the cassette said removable chamber having side walls and a base defined by a membrane; and
means for supporting the removable chamber above the first member in a first position and a second position, wherein the first position provides sufficient spacing between the chamber and the first member so as to not permit fluid transfer from the chamber to the body of absorbent material, and wherein the second position provides for contact between the membrane of the removable chamber and the first member to thereby fluid transfer from the chamber to the body of absorbent material;
b) placing said sample and a detection analyte in the removable chamber of the flow-through assay device with the removable chamber disposed in the first position so as to not permit fluid transfer from the chamber to the body of absorbent material, wherein the detection analyte consists of one or more detection compounds bound to a detectable element and wherein if a predetermined reagent is present in said sample said one or more detection compounds binds to the pre-determined reagent;

c) allowing a sufficient period of time to pass for the detection analyte to bind to the pre-determined reagent, if present in said sample;

d) depressing the chamber to the second position to thereby contact the base of the removable chamber with the porous membrane;

e) allowing fluid transfer from the removable chamber to the body of absorbent material such that the pre-determined reagent if present in the sample binds to the one or more capture analytes bound to the porous reaction membrane, thereby forming a complex between the detection analyte, pre-determined reagent and one or more capture analytes;

f) removing the removable chamber; and g) detecting the complex formed.

11. The method as claimed in claim 10 wherein the porous reaction membrane is washed with a buffer before detecting the detection analyte.

12. The method according to claim 10, wherein particulate materials are removed from the sample by virtue of the membrane in the removable chamber acting as a filter.

13. The method as claimed in claim 10, wherein the membrane defined at the base of the removable chamber is a hydrophobic membrane and wherein a wetting agent is applied to the contents of the chamber such that fluid transfer occurs when said hydrophobic membrane contacts the first porous reaction membrane.

14. The method according to claim 10, wherein the detection compound consists of one or more antibodies or antigens.

15. The method according to claim 14, wherein the detection compound consists of two or more antibodies bound to a detectable element.

16. The method according to claim 14, wherein at least one antibody is a control antibody.

17. The method according to claim 10, wherein the detectable element is selected from the group consisting of colloidal gold particle, latex bead, coloured dye and colloidal carbon.

18. The method according to claim 10 wherein the sample is free of unwanted analytes that may interfere with the binding of the pre-determined reagent to the capture analyte on the porous reaction membrane.

19. The method according to claim 10, wherein the sample is a body fluid.

20. The method according to claim 10, wherein the sample is a microbial extract or a plant extract.

* * * * *